(12) United States Patent
Jeketo

(10) Patent No.: US 10,416,124 B2
(45) Date of Patent: Sep. 17, 2019

(54) ULTRASONIC TESTING APPARATUS

(71) Applicant: ROLLS-ROYCE plc, London (GB)

(72) Inventor: Alejandro Jeketo, Matlock (GB)

(73) Assignee: ROLLS-ROYCE plc, London (GB)

(*) Notice: Subject to any disclaimer, the term of this patent is extended or adjusted under 35 U.S.C. 154(b) by 80 days.

(21) Appl. No.: 15/356,399

(22) Filed: Nov. 18, 2016

(65) Prior Publication Data

US 2017/0146494 A1 May 25, 2017

(30) Foreign Application Priority Data

Nov. 19, 2015 (GB) .................... 1520388.8

(51) Int. Cl.
*G01N 29/30* (2006.01)
*G01N 29/28* (2006.01)
*G01N 29/44* (2006.01)
*G01N 29/04* (2006.01)
*G01N 29/07* (2006.01)
*G01N 29/24* (2006.01)
(Continued)

(52) U.S. Cl.
CPC .............. *G01N 29/30* (2013.01); *G01H 1/00* (2013.01); *G01N 29/043* (2013.01); *G01N 29/07* (2013.01); *G01N 29/2418* (2013.01); *G01N 29/2462* (2013.01); *G01N 29/265* (2013.01); *G01N 29/28* (2013.01); *G01N 29/343* (2013.01); *G01N 29/4418* (2013.01); *G10K 11/24* (2013.01); *G01N 2291/044* (2013.01); *G01N 2291/0425* (2013.01); *G01N 2291/0427* (2013.01); *G01N 2291/101* (2013.01); *G01N 2291/102* (2013.01); *G01N 2291/2693* (2013.01)

(58) Field of Classification Search
CPC ...... G01N 29/30; G01N 29/043; G01N 29/07; G01N 29/2418; G01N 29/2462; G01N 29/28; G01N 29/343; G10K 11/24
See application file for complete search history.

(56) References Cited

U.S. PATENT DOCUMENTS 3,934,460 A 1/1976 Sherwin et al.
5,241,287 A 8/1993 Jen
(Continued)

FOREIGN PATENT DOCUMENTS

AU 2013 200 063 B2 2/2014
EP 1 214 910 A1 6/2002
(Continued)

OTHER PUBLICATIONS

Freschi et al., "Analyzing the total structural intensity in beams using a homodyne laser doppler vibrometer", Jun. 26, 2000, Available Online <http://downloads.hindawi.com/journals/sv/2000/952482.pdf>, accessed May 2018.*
(Continued)

*Primary Examiner* — David Z Huang
(74) *Attorney, Agent, or Firm* — Oliff PLC

(57) ABSTRACT

An apparatus for use in Ultrasonic testing, and a method of inspection or testing using the apparatus. The ultrasonic testing tool includes an elongate connector arranged between a transducer and a tip or contact head for contact with the component to be tested. The elongate connector carries soundwaves produced by the transducer between the transducer and the contact head.

13 Claims, 7 Drawing Sheets

(51) Int. Cl.
  *G01N 29/265* (2006.01)
  *G01N 29/34* (2006.01)
  *G10K 11/24* (2006.01)
  *G01H 1/00* (2006.01)

(56) References Cited

U.S. PATENT DOCUMENTS

| | | |
|---|---|---|
| 5,289,436 A | 2/1994 | Terhune |
| 2013/0260469 A1 | 10/2013 | Djordjevic et al. |

FOREIGN PATENT DOCUMENTS

| | | |
|---|---|---|
| EP | 2 221 615 A1 | 8/2010 |
| JP | 2007-212358 A | 8/2007 |
| WO | 2004/020993 A2 | 3/2004 |

OTHER PUBLICATIONS

Lawrie et al., "Edge wave and resonance on elastic structures: an overview", 2012, Brunei University, pp. 1-17 (Year: 2012).*
Norris et al., "Flexural edge waves and Comments on a new bending wave solution for the classical plate equation", 1998, The Journal of the Acoustical Society of America 104, 2220-2222, pp. 1781-1784 (Year: 1998).*
Lagasse et al., "Acoustic Surface Waveguides—Analysis and Assessment," IEEE Transactions on Microwave Theory and Techniques, 1973, vol. 21, No. 4, pp. 225-236.
Feb. 3, 2017 Search Report issued in European Patent Application No. 16 19 9524.
Mar. 23, 2016 Search Report issued in British Patent Application No. 1520388.8.

* cited by examiner

ULTRASONIC TESTING APPARATUS

BACKGROUND OF THE INVENTION

The present invention relates to the field of Non-Destructive Evaluation of components, and in particular to a tool for use in Ultrasonic testing. The invention also relates to a method of inspection or testing using such a tool.

Non-Destructive Evaluation (NDE) encompasses a range of techniques enabling inspection and evaluation of the properties of a material or component without causing damage to the component. As such, NDE techniques are of widely used in the engineering industry during the routine inspection and maintenance of components and systems, in particular safety critical systems.

In the Aerospace industry safety checks and inspections are commonly carried out on components immediately after their manufacture and regularly through their lifespan. Various NDE techniques are employed depending on the component being inspected. In the case of components having safety-critical surfaces, Fluorescent Penetrant Inspection (FPI) or Eddy Current Testing (ECT) are often used with great effectiveness.

However, because of the hostile environment in which they operate, some aerospace components are coated with protective materials that may limit the effectiveness of FPI and ECT. For example, some coatings absorb the eddy currents used during ECT, preventing any penetration into the underlying component and thus rendering the inspection inadequate. Equivalent limitations are encountered when attempting FPI on coated components.

As a result, it is necessary to remove the coating from individual components prior to testing. This can be difficult, especially once the engine has been run. Once the testing is complete, the components need to be re-coated before returning to service. This process takes a significant amount of time and effort.

It is an aim of the present invention to provide a device and method that overcomes, or at least mitigates, some or all of the above problems, specifically by opening up the possibility of using an inspection method appropriate for coated surfaces on complex components without prior coating removal.

BRIEF SUMMARY OF THE INVENTION

According to a first aspect of the invention there is provided a method of inspecting a component, the method comprising the steps of spacing an ultrasonic transducer from a contact head, using an elongate connector arranged between the transducer and the contact head, wherein the elongate connector carries soundwaves produced by the transducer between the transducer and the contact head; placing the contact head into contact with a surface of the component to be tested; transmitting a wavepacket signal from the transducer along the elongate connector and into the component to be tested; and monitoring for reflection of the signal from within the component using the detector.

The component may be a sharp edged component.

The contact head may be placed into contact with the component adjacent a sharp edge, The soundwaves produced by the transducer may excite a flexural wave in a sharp edge of the component.

The detector may monitor the deflection of an edge of the sharp edged component.

The detector may be spaced from the contact head.

The detector may comprise a laser vibrometer.

A defect may be detected by the method when the detector first detects an incident wave directly generated in the component by the signal from the transducer and subsequently detects a reflected wave of similar magnitude to the incident wave.

The detector may monitor an area that is no more than 1 mm wide.

The method may further comprise the step of transmitting coupling media to the interface between the contact head and the component to be tested.

During inspection, the contact head may be held in a fixed position on the component to be inspected.

The soundwaves may comprise a signal with a frequency from 500 kHz to 2 MHz.

The method may be used for inspecting an annular component such as a seal fin.

The invention also provides Ultrasonic Testing (UT) apparatus comprising a transducer, a contact head, for contact with the component to be tested, and an elongate connector arranged between the transducer and the contact head to space the transducer from the component, wherein the elongate connector carries soundwaves produced by the transducer between the transducer and the contact head.

The contact head has an end surface that may be smaller, in at least one dimension, than an emitting surface of the transducer. In some embodiments, the total area of the end surface of the contact head may be smaller than the emitting surface of the transducer.

In the context of the invention 'elongate' is taken to mean that the connector is significantly longer than it is wide. The connector may, for example, be at least 5 times as long as it is wide, or even at least 10, 15, 20, 25 or 30 times as long as it is wide.

The smallest dimension of the end surface may be less than or equal to 1 mm.

The area, or the total area, of the end surface of the contact head may be smaller than the emitting surface of the transducer.

The soundwaves may comprise a signal with a frequency from 500 kHz to 2 MHz, for example around 1 MHz.

The apparatus may further comprise a fixing device for securing the contact head in contact with component to be tested during use. For example, a clamp or similar device could be incorporated into the contact head or provided as a further separate component The apparatus may further comprise a conduit for delivering coupling media to the interface between the contact head and the component to be tested and/or the contact head may comprise an acoustic matching layer.

The elongate member may comprise a damping or acoustic matching material, for example adjacent the transducer, to reduce or eliminate internal reflection of energy within the elongate member.

The apparatus may further comprise a detector for detecting oscillations or waves in the component to be tested, for example oscillations in a tip of a component.

The detector may comprise a laser vibrometer or other component, such as a further elongate member and transducer as described above, for monitoring deflection of the tip of a component. Incident waves, emitted directly from the contact head, and waves reflected from an end of the component of a defect therein could be detected. Alternatively, the contact head of the elongate connector used to carry the soundwaves to the component could also be used as an interface for the detector. The same elongate connector and transducer may then be used to transmit an input wave and detect resulting waves in the component.

The area monitored by the detector, ie the physical contact point or width of a laser beam, may be no more than 1 mm wide.

The invention also beneficially spaces the transducer from the surface of the component to be inspected, while still allowing contact UT to be used.

The contact head may comprise an acoustic matching layer and/or a wear resistant layer.

The contact head may not be fixed in position relative to the component to be tested. For example, the contact head may be free to be moved or scanned across a component to be tested or inspected.

The elongate connector may be deformable. The elongate connector may comprise a flexible non-acoustically attenuative material, for example a shape memory alloy. Alternatively, the elongate connector may comprise one or more lockable joints along its length.

The ultrasonic testing tool may further comprise a conduit for delivering coupling media to the interface between the acoustic matching layer and the component to be tested. The coupling media may, for example, be water or a viscous gel.

The cross section of the elongate connector may vary along its length.

The described apparatus may be used in a method as previously described.

The invention also provides a method of inspecting a sharp edged component, the method comprising the steps of taking testing apparatus as previously described, placing the contact head into contact with a surface of the component to be tested, transmitting a wavepacket signal from the transducer along the elongate connector and into the component to be tested; and monitoring for reflection of the signal from within the component using the detector.

The contact head may be placed into contact with the component adjacent a sharp edge, and the detector may monitor the deflection of an edge of the sharp edged component, for example at a particular point on the edge.

The detector may be spaced from the contact head, to monitor both the incident wave and reflections from any defects.

A defect may be detected when the detector first detects an incident wave directly generated in the component by the signal from the transducer and subsequently detects a reflected wave of similar magnitude to the incident wave.

The method may be used for inspecting an annular or circumferential component, such as a seal fin, in which case reflections from the end of a component will not arise.

The invention also provides a method of inspecting a component comprising the steps of: taking a testing tool as previously described, placing the contact head into contact with a surface of the component to be tested, and moving the contact head across the surface of the component.

The method may be applied in the inspection of an annular component. The component may be inspected from the outside, with the contact head moved across an outer surface of the component. Alternatively, the component may be inspected from the inside, with the contact head moved across an inner surface of the component. In this case, the transducer of the testing tool may remain located at or adjacent the central axis of the component during the inspection.

Wherever practicable, any of the essential or preferable features defined in relation to any one aspect of the invention may be applied to any further aspect.

Accordingly, the invention may comprise various alternative configurations of the features defined above.

BRIEF DESCRIPTION OF THE DRAWINGS

Practicable embodiments of the invention are described in further detail below by way of example only with reference to the accompanying drawings, of which.

DETAILED DESCRIPTION OF THE INVENTION

Ultrasonic Testing (UT) is a known technique that is often used to detect cracks and defects in components to ensure safety and performance. In one method, known as contact UT, a transducer is placed in contact with the component to be inspected. Sound transmission is achieved via a coupling medium (gel or water depending on the application). The inspected volume is usually limited to a small region beneath/adjacent to the transducer at the point of contact, which may be moved or scanned along surface during the inspection. Significantly, the technique is not affected by the presence of a coating on the surface of the component.

Given the problems that exist with using FPI and ECT on coated components, UT was investigated for the inspection of gas turbine engine assemblies at overhaul. Specifically, there was a desire to use the technique to inspect the seal fins of aero engines, where cracking may potentially occur. However, for small components such as the seal fins of aero engines, there simply isn't space to apply a transducer to an exposed surface.

Figure 1:
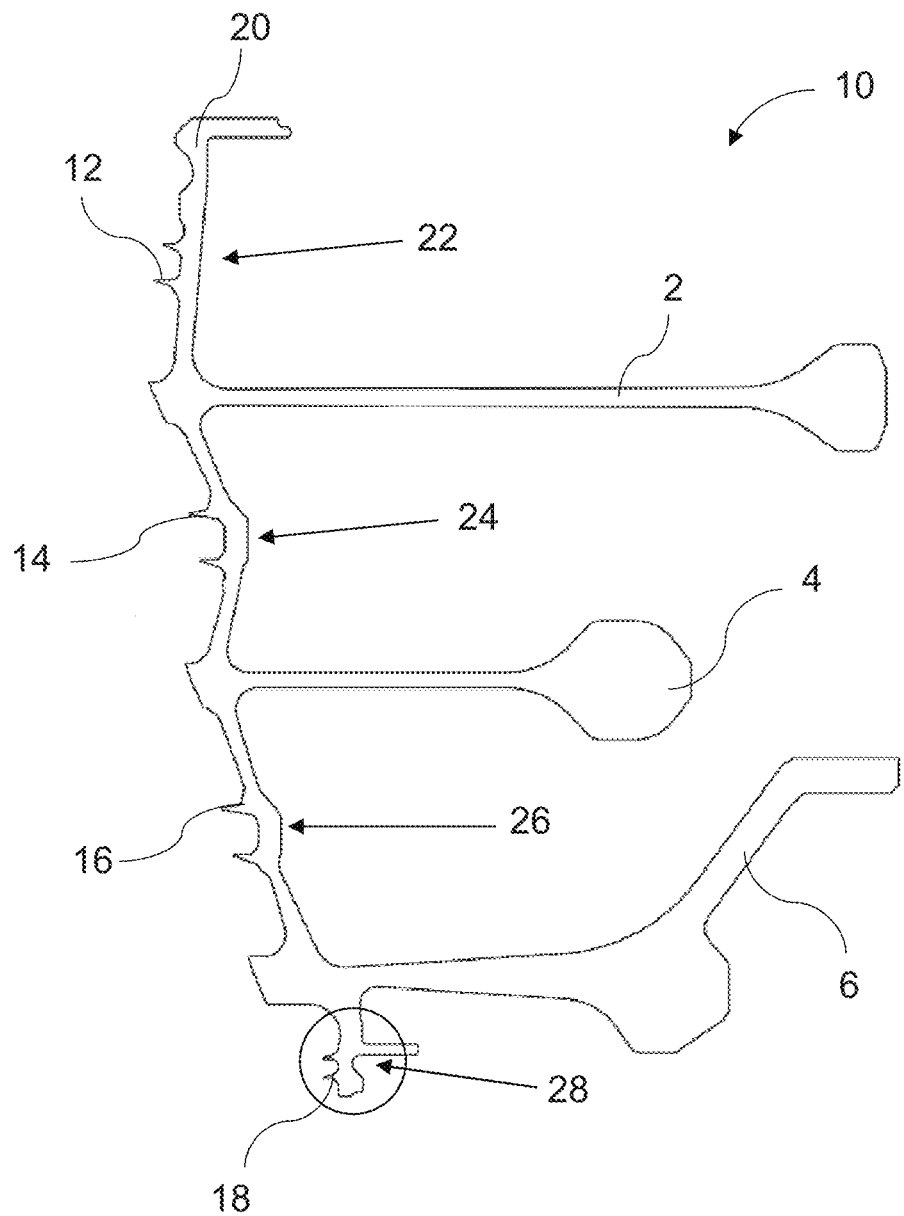
FIG. 1 shows a cross section of part of an aero engine.

By way of example, FIG. 1 shows a cross section through the first three stages 2,4,6 of a compressor drum 10. Closely spaced seal fins 12,14,16,18 can be seen on the outer surface of the compressor 10. Due to their close spacing, it is not possible to introduce a contact probe or transducer to the fins 12,14,16,18 directly in order to conduct an inspection. It is possible to inspect the fins 12,14,16,18 from the inside of the compressor drum 10, provided that a generally flat surface is accessible on the opposite side of the wall 20 of the compressor drum 10 opposite the fins 12,14,16,18.

It should be clear from FIG. 1 that access to the interior surfaces 24,26 between the compressor stages 2,4,6, as well as the interior surface 22 above the stages as shown is restricted, such that an operator would struggle to insert a contact probe/transducer to inspect the surfaces. In particular, the lowermost stage 6 presents a convoluted path to the area 26 opposite one set of fins 16. The manipulation necessary to insert and align the equipment poses a significant handling damage risk to the component.

The region indicated 28, at the lowermost part of the compressor 10 as indicated, presents its own set of problems, as will be explained later.

Figure 2:
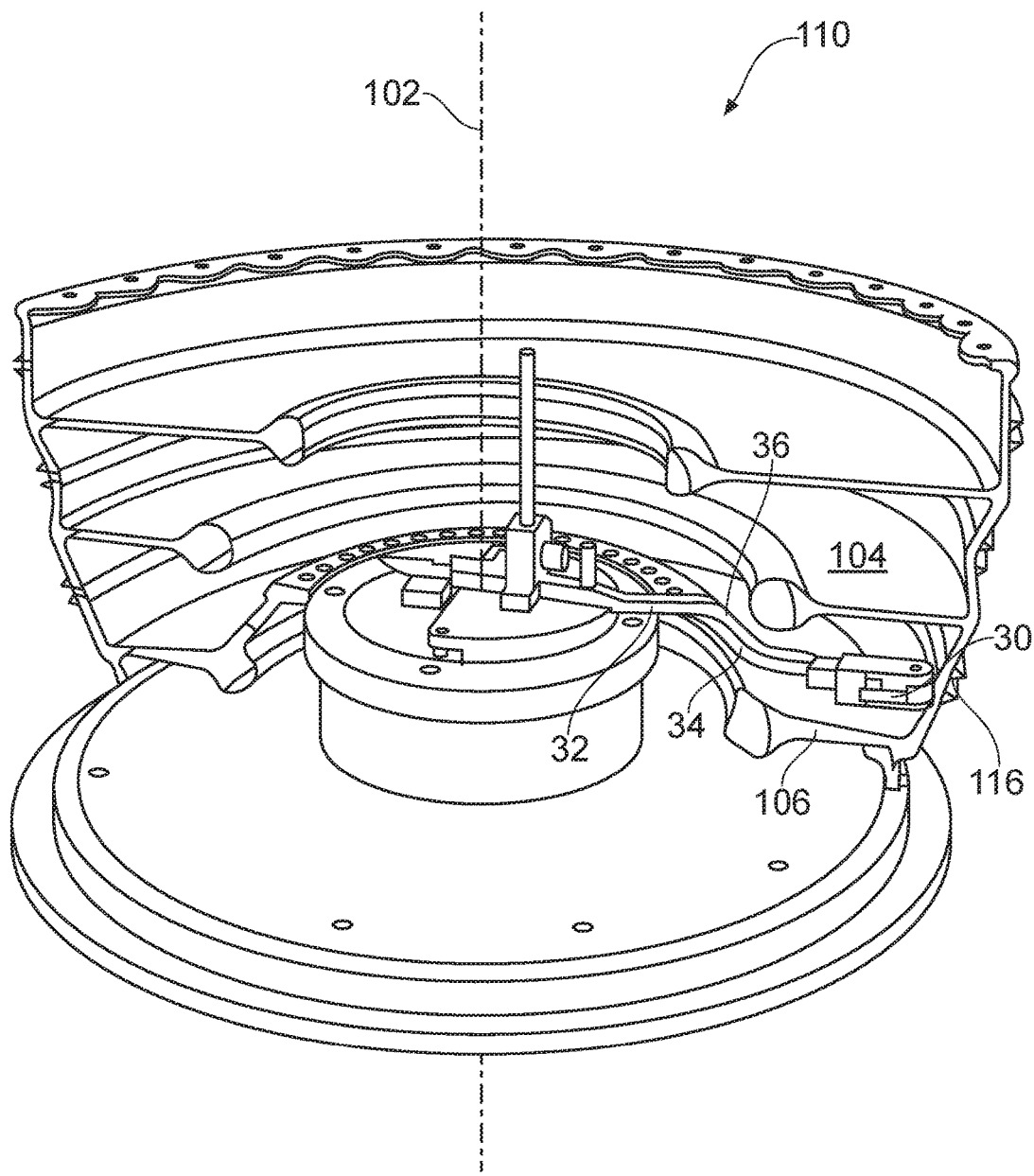
FIG. 2 shows a stage of development of one embodiment of the present invention.

One approach to address the problem of delivering contact probes/transducers and the required coupling media to the required inspection is shown in FIG. 2.

In particular, FIG. 2 shows a section through stages 1-3 of the high pressure compressor (HPC) 110 with the seal fins 116 between two adjacent stages 104,106 being inspected.

The solution illustrated in FIG. 2 is to provide a small transducer and a coupling medium delivery system, together designated 30, on one end of an arm 32 which extends from the axis 102 of the compressor to the radially outer position where the seal fins are located. A delivery tube 34 for delivering coupling media in the form of water or gel extends along the length of the arm 32.

The shape of the adjacent compressor disks, in particular the lowermost disk 106 as shown, means that the passage from the axis 102 to the radially outer part of the compressor 110 is not straight. A bend 36 is provided in the arm 32 to account for the shape of the lowermost disk 106, and allow the transducer to be appropriately positioned. However, the combined transducer and coupling media delivery system 30 remains relatively large compared to the gap, and must still be accurately threaded through a narrow passageway with a significant degree of curvature. This must be done remotely from the opposite end of the arm 32, making precise positioning difficult and leading to likely contact with the engine components which could potentially damage the transducer and coupling media delivery system 30 during deployment and/or removal. The entire operation is therefore cumbersome and difficult.

Furthermore, the solution illustrated in FIG. 2 is not universally applicable. The internal geometry found in certain aero engines, even across equivalent components, can be considerably tighter. As a result, the space between compressor stages is greatly reduced, and/or the resulting passageways are more convoluted. Very small transducers would be required to fit into such tight areas of significant curvature. However, suitably sized transducers that provide the necessary ultrasonic performance are not commercially available.

In practice, the space constraints either prohibit the introduction of a transducer at the appropriate location, or require the use of a smaller transducer, with a correspondingly lower power output, than would be desirable for the inspection operation. There is also significant risk of damage to a transducer or contact probe as it is fed through the relatively narrow gaps that exist within such components.

For both of these reasons, the delivery of contact probes/transducers to the inspected area is difficult, if not impossible, for these components. As a result, it would still typically be necessary to break down aero engines to allow the inspection of individual components following the method of FIG. 2, and to subsequently reassemble the inspected components. This requires significant amount of work, and thus greatly increases the cost and duration of an inspection operation.

Furthermore, it is increasingly common for compressors to incorporate single piece bladed drums. Without the option to break these components down, the only approach would be to remove the coating and inspect using FPI or ECT as previously described, with the associated cost and time implications.

Further problems with the solution of FIG. 2 will be explained with reference to FIG. 3, which shows a cross-section of part of one stage in greater detail.

Figure 3:
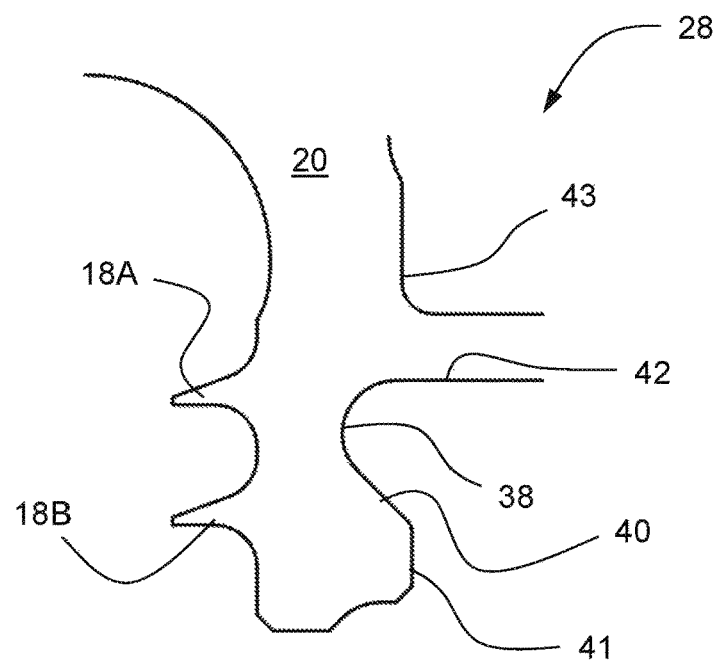
FIG. 3 shows detail from FIG. 1, showing an area for inspection.

Specifically, FIG. 3 shows an enlarged view of the region marked 28 in FIG. 1. The seal fins 18A,18B, are small and are located close together, meaning that contact and therefore inspection from the exterior of the wall 20 is not possible, for the reasons set out previously. As can also be seen clearly in FIG. 3, there is a significant curvature on the surface of the wall 20 opposite the seal fins 18A,18B. The result of this tight spacing and curvature is that no readily accessible surface exists for a probe/transducer to contact on the inside of the compressor drum either.

To recap, with reference to FIG. 1, although access to certain areas 22,24,26 on the interior of the compressor drum 10 is restricted, there do exist readily accessible, generally flat, areas allowing reliable contact with a transducer or probe of the Type shown in FIG. 2. In contrast, in the area 28 shown in FIG. 3, the base 38 of the curved region is too small and too confined by surrounding surfaces 40,42 to be accessed by an appropriate transducer/probe, even where the compressor is broken down to simplify access to individual components. Some inspection of the lower seal 18B may be possible from flatter surface 41, which is below the lower fin 18B in the inside of the component. Ultrasonic energy is typically emitted at an angle of around forty-five degrees, which may be sufficient to reach the lower fin 18B. However, the upper fin 18A is spaced too far from another flat surface 43 to make the same approach possible.

Figure 4:
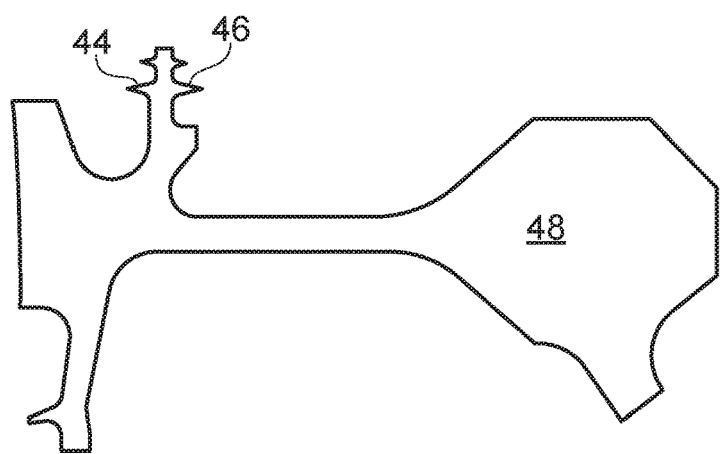
FIG. 4 shows a cross section of another component for inspection.

A similar problem can occur when seal fins 44,46 are formed in opposing pairs on opposite sides of a component 48, for example as shown in FIG. 4. This causes great difficulty when trying to inspect either set of fins 44,46 since no accessible flat surface is provided.

Figure 5:
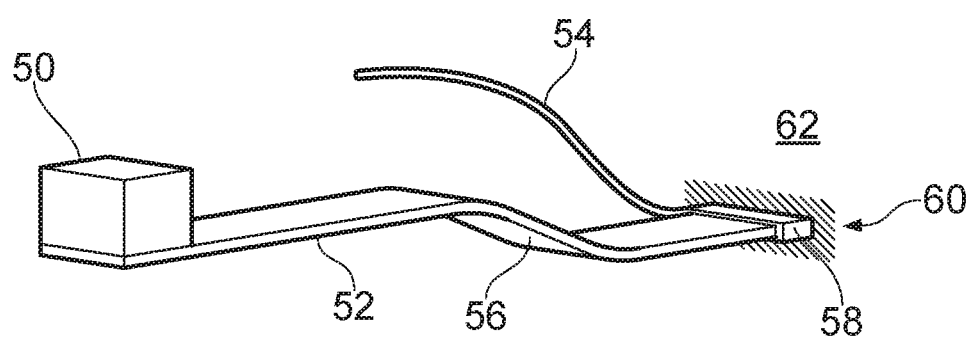
FIG. 5 shows an example of a waveguide according to one embodiment of the present invention.

FIG. 5 shows an example of the first embodiment of the present invention. A transducer 50 is connected to a first end of an elongate connector 52. At a second, opposite, end of the connector 52, a contact head 58, comprising an acoustic matching material and a wear layer, is provided for contact with an area 60 of a component 62 to be inspected. A coupling media delivery system 54, in the form of a flexible tube, is also provided to deliver water, gel or some other appropriate coupling media to the interface between the contact head 58 and the component.

In use, the transducer 50 transmits sound into the elongate connector 52 such that a guided wave travels along the connector 52 to the location/area 60 for inspection. The wave is set up to only be reflected by defect(s) in the component 62. The wave moves along the length of the elongate connector 52 and into the component 62 to be inspected, i.e. in a circumferential direction for an annular component. The acoustic matching material of the contact head 58 has an acoustic impedance between that of the elongate connector 52 and the component 62 to be inspected. This permits sound transmission into the component 62 at the correct contact pressure and orientation, thereby reducing losses, and helps to avoid damaging the component 62.

The elongate connector 52 effectively guides the ultrasonic energy between the transducer 50 and the area 60 to be inspected. As illustrated in FIG. 5, an 's' bend 56 is provided in the elongate connector 52 to cope with the convoluted passageways that exist between compressor stages. The guiding effect of a curved elongate connector 52 remains effective provided that the radius of curvature along its path remains significantly greater than the ultrasonic wavelength. Problems do arise if the wavelength used is of the same order of magnitude as the radius of curvature. For example, with a 1 MHz shear wave travelling through the elongate connector at a speed of 3260 m/s, the radius of curvature would need to be significantly greater than 3.26 mm. In this example, a lower limit of approximately 20 or 30 mm would likely be sufficient.

It should be understood that by selecting appropriate materials for the elongate connector 52, to vary the speed of transmission, and by varying the frequency applied, different limits on the radius of curvature could be achieved.

FIG. 5 shows the elongate connector 52 as a curved flat plate of uniform dimensions. The flat plate provides a thin contact to aid access into tight spaces, such as the small gap between the surfaces 40,42 shown in FIG. 3. However, there is no need for the elongate connector 52 to have this particular cross-section. Indeed, there is no need for the cross-section of the elongate connector 52 to be uniform along its length. It may be preferable for the footprint at the contact head 58 to be significantly smaller than the contact area with the transducer 50, particularly when small or very confined areas 60 are to be inspected.

As well as allowing access to the small base 38 of curved internal surfaces as shown in FIG. 3, the small contact head 58 opens up the possibility of inspecting features from the outside of the wall 20. For example, the contact head 58 could fit between the seal fins 18A,18B in a way that a standard probe, or the system of FIG. 2, could not.

Where multiple features are to be measured, such as the double rows of seal fins 18A,18B in FIG. 3, the ability to contact the opposite surface 38 between the fins 18A,18B means that the forty-five degree spread of the ultrasonic energy allows measurement of both fins 18A,18B simultaneously in a way that the size of the conventional transducer makes impossible.

As illustrated in FIG. 5, the contact head 58 of the elongate connector 52 is not fixed to the component 62. A key benefit of this is that it allows the contact head 58 to be 'scanned' over the surface of what is being inspected.

The wear layer of the contact head 58 and the accompanying coupling media delivery system 54 permit the contact head 58 to be moved or scanned along the surface of the component 62 such that the inspection volume 60 can be moved and complete inspection coverage of the component 62 can be achieved. Among other things, this makes it possible to image the part and create a defect map and to directly control the volume of the material that is being interrogated. The invention can be readily used in the field with existing NDE personnel without additional training, and the data interpretation is much easier and more robust.

When inspecting an annular component internally, in a similar manner to shown in FIG. 2, the invention provides an additional advantage in that the transducer 50 can remain relatively stationary, effectively just rotating around the axis 102, while the contact head 58 is scanned along the surface of the component 60.

The placement of the coupling media will have minimal impact on the propagating wave as long as the correct wave mode is excited (e.g. Shear Horizontal, SH) and as long as the attachment between the delivery system 54 and the elongate connector 52 doesn't involve bolts or welding or similar fixings that would disrupt its cross-section.

The invention as described above allows the precise delivery of bulk waves to areas that would otherwise be inaccessible to this type of inspection. The use of bulk waves provides increased sensitivity compared to that provided by a guided wave approach, which is of particular benefit when small cracks or flaws in a component need to be detected reliably.

The inspection is relatively insensitive to temporal resolution. This means that limitations on the piezo-electric elements are effectively eliminated, allowing the use of lower frequency (eg sub-MHz) transducers, and dispersion losses are less problematic The transducer won't be required to operate in such hostile environments. It may therefore be kept cool more easily, so attenuation can be more readily managed, and no longer needs to be high-temperature capable or corrosion resistant.

Allowing inspection from the interior of a compressor also means that the inspection itself will be in a less hostile environment, so 'normal' coupling media such as viscous gels, which are not typically suitable for more hostile environments, can be used In addition, the invention facilitates 'on-wing' NDE of engine components. HS&E legislation prevents the use of ultrasonic transducers (which have to be excited with anything up to 250 V) in environments where a fire or explosion could be caused by a spark etc. An aero engine is one such environment. The invention could remove the transducer from the critical zones as defined by this legislation, and therefore allow inspections to be performed without taking an engine off-wing and stripping it down.

The abovementioned inspection method can broadly be referred to as a 'bulk wave' inspection method. An alternative inspection method utilising a similar waveguide will now be described. The alternative method makes use of a newly discovered flexural 'edge mode' of vibration that can be generated in a sharp edge or tip of a component such as the seal fins of compression drums or discs found in aero engines. A guided wave is essentially generated within the specimen, having passed from the waveguide, and is mode-converted into a very specific type of wave, an 'edge wave', that can only exist in sharp edged geometries such as seal fins.

Figure 6:
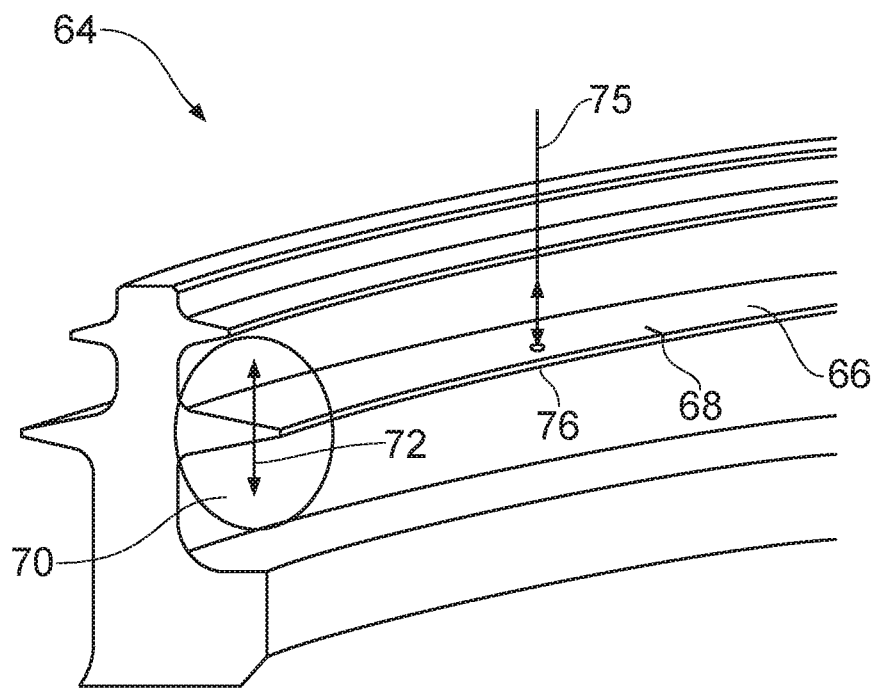
FIG. 6 shows a segment of a component used in development of a second embodiment of the present invention.
Figure 7:
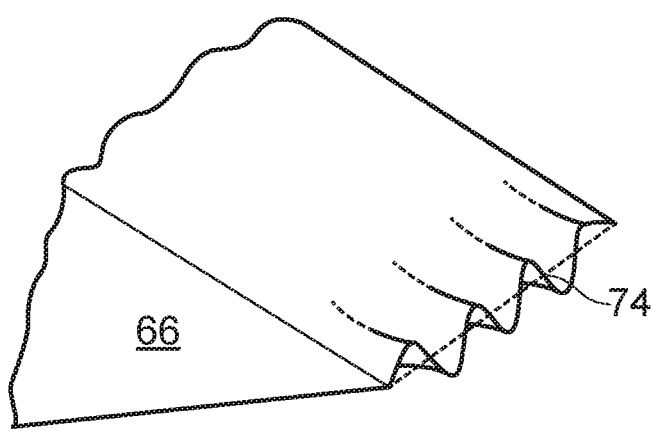
FIG. 7 shows detail of an edge portion of the segment from FIG. 6.

FIG. 6 shows a 160 mm long segment 64 of a component, comprising four seal fins 66, that was used during development of the alternative method. A radial notch 68 around 0.75 mm in length was machined into the tip of each of the four fins 66 to represent a defect. In order to excite a flexural wave in each fin, a shear transducer (not shown) was then placed on the end cross-section 70 of the component segment 64 to generate shearing motion in the fin 66 as indicated by arrow 72. The shearing motion 72 in turn excites a flexural edge wave 74 in the fin 66 as illustrated in FIG. 7. The motion of the edge wave 74, and thus its detection capability, is confined to the edge portion of the component, making it a very efficient form of guided wave. The acoustic losses to the environment are minimal, but the sensitivity to defects is excellent.

To receive the signal, a laser vibrometer 75 was used to monitor the out of plane velocity of the fin tip at a location 76 between the end of the segment and the notch 68. The laser vibrometer is sensitive to any wave packet passing the monitoring position, and therefore the received signal will see first the incident wave passing the monitoring position, then the reflection from the defect, and finally the reflection from the end of the segment. The shear transducer was operated at 1 MHz for best compatibility with the laser vibrometer 75.

Figure 8A:
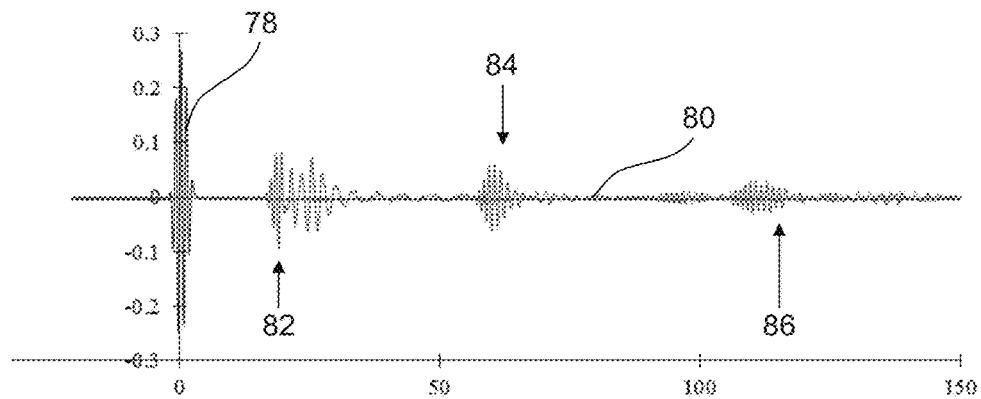
FIG. 8A to 8C are graphs showing vibration readings obtained during development of the second embodiment.
Figure 8B:
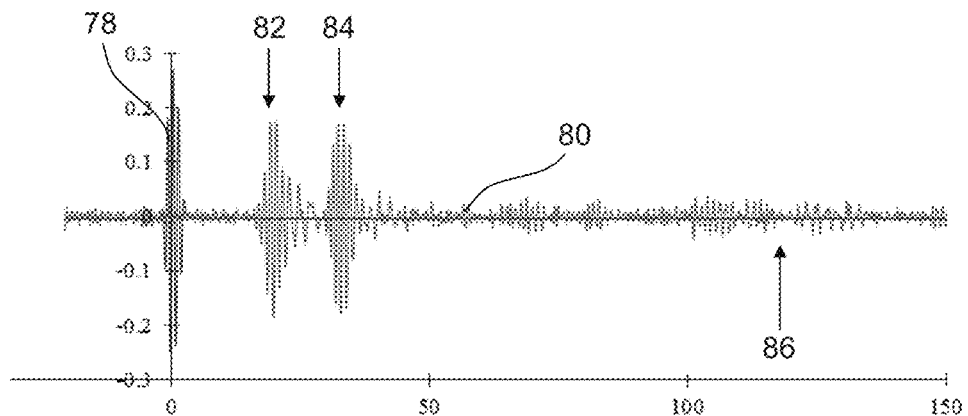
Figure 8C:
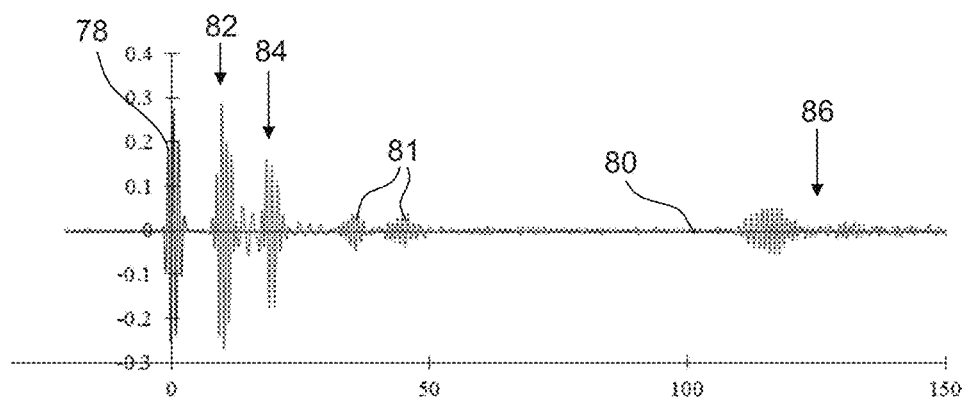

Traces of the transducer input 78 overlaid with the fin tip out of plane velocity 80 of three different fins 66 measured by the laser vibrometer are provided in FIGS. 8A to 8C. The vertical axes in FIGS. 8A to 8C show the amplitude of the input and velocity of the resulting wave, with the horizontal axes showing the time in μs. In each case, the incident wave, the defect reflection and the end reflection were detected in sequence as anticipated. However, FIG. 8C shows that, in one instance, two additional second reflections 81 were also detected.

The expected arrival time of the incident wave, the defect reflection and the end reflection (which arises because only a segment of a full component was used for the testing) was calculated for each fin 66 based on the particular notch 68 location and the group velocity of the edge nodes, which had been determined to be around 2500 ms$^{-1}$. The incident wave arrival time 82 was calculated at 20 µs, 18 µs and 9.6 µs respectively for the three different fins. The defect reflection arrival time 84 was similarly calculated as 60 µs, 32 µs and 16.8 µs, and the time for the end reflection 86 was calculated as 116 µs, 118 µs and 126 µs. As can be seen, these predicted times 82,84,86 correlate well with the oscillations actually detected by the laser vibrometer.

The results illustrated in FIGS. 8A to 8C demonstrate the existence of the anticipated edge modes, and their excellent sensitivity to defects. In each case the defect reflection is of a similar magnitude to the incident wave illustrating the almost complete reflection of energy, indicating that the wave modes must be highly localised as anticipated. It is also worth noting that the diminished end reflection is likely a result of the notch/defect 68 blocking energy reaching the end.

The experimental results thus show that the edge modes exist and behave as predicted, and are very promising for screening for defects. However, the methodology described above is not viable in practice because the end cross-section 70 used for excitation with the shear transducer will not be available in practice. The only available access for closed circular features such as seal fins 66 is at the edges of the individual fins 66.

In order to excite the flexural edge modes from this position, the fin tips must be displaced laterally. A key problem with this is that the displacement must be applied through a footprint that is far smaller than the wavelength of the flexural edge mode to be generated. An acceptable maximum footprint width is typically around one fifth of the wavelength.

The solution, according to the present invention, is to use of an elongate connector, or waveguide, to focus the energy for transmission. The elongate connector 88, shown in FIG. 9, takes the form of a waveguide, which has a transducer element 90 at one end and a tip at the other. The waveguide 88 is approximately 165 mm long and 5 mm in diameter along the majority of its length. In use, the transducer element 90 will send a longitudinal wave down the waveguide 88, and the resulting displacement of the wave guide tip will excite the flexural edge mode 74 as illustrated in FIG. 7.

The following table shows the wavelengths of the edge modes at different frequencies.

| Frequency | Wave Length [mm] | Maximum Transducer Footprint [mm] |
|---|---|---|
| 100 kHz | 32.05 | 6.41 |
| 200 kHz | 6.94 | 1.39 |
| 300 kHz | 4.88 | 0.98 |
| 400 kHz | 3.90 | 0.78 |
| 500 kHz | 3.30 | 0.66 |
| 1 MHz | 1.98 | 0.40 |
| 2 MHz | 1.17 | 0.34 |
| 3 MHz | 0.85 | 0.17 |

The width or diameter of the footprint for a transducer operating at any of the frequencies quoted above should not exceed the listed value. At preferable frequencies, around 500 kHz or higher, it should be clear that the transducer footprint through which the modes are excited must be of the order of <1 mm diameter. The same restriction would also apply to any receiving transducer. A transducer spanning several wavelengths will simply see the average displacement which will be zero.

Figure 9:
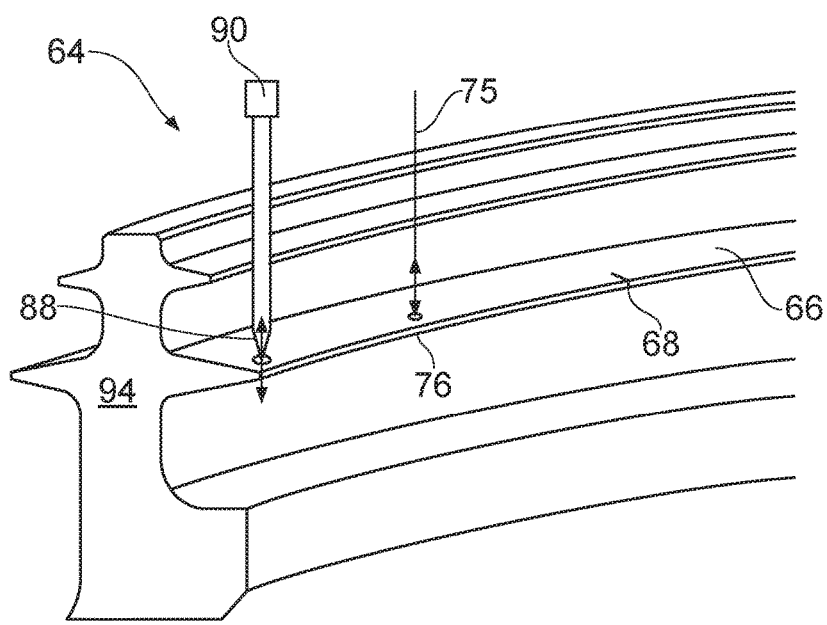
FIG. 9 shows a waveguide in use on the component segment from FIG. 6.

The effectiveness of the proposed waveguide 88 was investigated, as illustrated in FIG. 9, using the same segment 64 of a component as discussed in relation to FIG. 6 above. For the purposes of testing, the waveguide 88 was placed and manually held in contact with the fin 66 in proximity to the point-like sensing area 76 of a laser vibrometer 75 which was again used to measure the passing incident wave and any further signals. An inspection frequency of 500 kHz was used to match the transducer element 90 of the waveguide 88.

The transduction point was chosen to be as near a first end 94 of the finite segment 64 as practicable to try and avoid confusion resulting from any end reflections from the first end 94. The rationale was that any end reflection from the nearby first end 94 of the segment 64 should simply merged with the incident wave packet, which is already distorted to a degree as it passes along the waveguide 88 and crosses the interface between the waveguide 88 and the fin 66.

Figure 10:
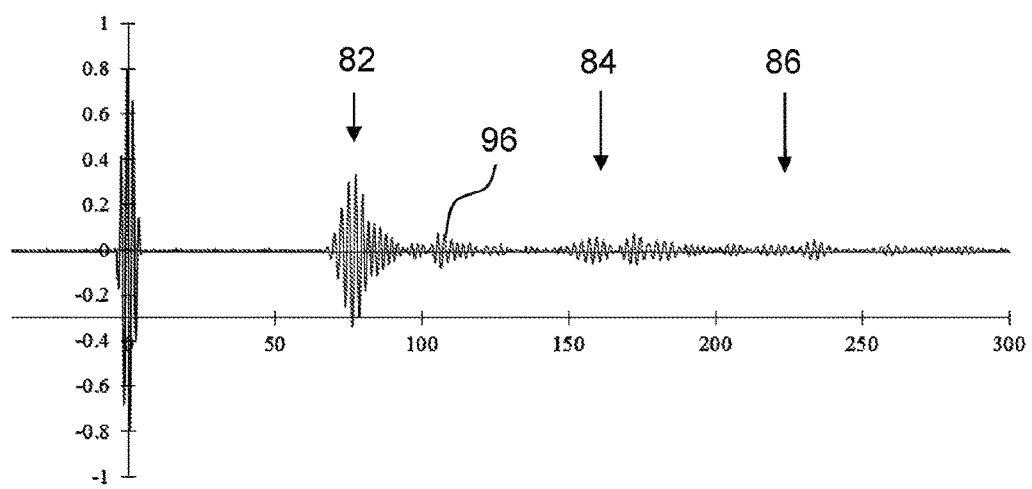
FIG. 10 is a further graph showing vibration readings obtained during development of the second embodiment.

A typical result from this experiment is shown in FIG. 10, which is similar to the graphs shown in FIGS. 8A to 8C. Once again, the predicted arrival times for the incident wave, defect reflection and end reflection 82,84,86 were calculated in advance for comparison with the results. In this instance, the incident wave arrival time 82 was calculated at 78 µs, the defect reflection arrival time 84 was calculated as 159 µs, and the end reflection arrival time 86 was calculated as 220 µs. It can be seen from FIG. 11 that the laser vibrometer 75 was able to identify the incident wave, defect reflection and end reflection at times corresponding to those predicted.

It should be noted that the quality of the signal in FIG. 10 could be significantly improved in practice. The end reflections from the first end 94 of the finite segment 64 and reverberations from the hand-held waveguide 88 'muddy' the signal making it more difficult to interpret. However, with complete circular components the end reflections cease to be a concern, and the reverberations from the waveguide 88 can be limited through an appropriate choice of materials.

Improved contact/connection with the fin 66, or other component, during use, for example through the use of a suitable coupling media and/or acoustic matching layer at the tip of the wave guide 88 would also improve results. A mechanical, clamp-on, design may also be provided to ensure that the tip remains in secure contact with a component during inspection, making results easier to obtain and more repeatable. No such steps were taken in obtaining the result shown in FIG. 10.

As discussed above, inspection of seal fins 44,46,66, especially when close together, can be problematic because accessible surfaces are not readily available. The method described above helps to address these problems by focussing on the more accessible tip portion of the fins 66, and taking advantage of a vibration mode that is specific to the tip portion.

The vibrations generated in the alternative inspection method have a number of benefits, such as:

They are highly localised to the fin tips and so will have good sensitivity to cracks at the tips.

The localisation means that little energy will leak into the surrounding structure and therefore are expected to propagate well.

They are non-dispersive above around 2 MHz and will be sufficiently non-dispersive for practical use above around 500 kHz.

They have group velocities approaching the shear velocity suggesting that reflected signals will be amongst the first arrivals, aiding interpretation.

Although high frequencies, of the order of 2-3 MHz, are expected to be optimal for this method described, the experiments discussed above were conducted at 500 kHz and 1 MHz and were found to be quite adequate. These lower frequencies advantageously allow a larger transducer footprint and will also reduce the number of modes present in the waveguide that may distort the signal.

The signals were shown to propagate very well along the component, in accordance with the theory. It is expected that the length of the drum circumference that can be examined from a single transducer location will be limited not by leakage or attenuation but from the internal reflection of the waveguide. For example, a wavepacket takes around 50 μs to travel the length of the wave guide 88. The wavepacket will be reflected, in part, internally within the wave guide 88 as well as being transferred to the fin 66 or component under testing. After 100 μs, the wavepacket will have travelled back up and down the waveguide 88, resulting in a second signal being transmitted into the test component 100 μs after the first. The second signal may mask the presence of any defect reflections passing the detection location 76 at a similar time. For an edge mode group velocity of 2300 ms$^{-1}$, the edge mode would travel 0.23 m before the second signal, which would equate to 0.115 m of screening length to allow for defect reflections to return to the laser vibrometer 75, receiving transducer or similar.

A longer delay could be provided by increasing the length of the waveguide 88, or by altering its material to one with a slower bulk wave velocity. Waveguide material may also be a consideration in mitigating the risk that tip causes damage the component coating. Internal reflections may also be reduced or eliminated through the incorporation of a suitable damping material at the end of the waveguide 88 adjacent to the transducer 90.

Providing a transducer that has its active element right at the tip would also address the problem. As previously discussed, this would likely limit the minimum achievable tip size and/or the power of the transducer in a way that is undesirable, but the benefits of avoiding internal reflection may outweigh this in certain circumstances.

Although a laser vibrometer 75 is described throughout for receiving the signals, it would also be possible to instead use a waveguide such as that proposed for transmission. As with transmission, the transduction area would need to be much smaller than the wavelength that is to be detected, and the problems of limited transmission through the tip of the guide and introduced signal distortion would need to be addressed, but approaches such as discussed above would be appropriate to mitigate these problems.

A laser vibrometer 75 does, however, have a similar, point-like, area of sensitivity and circumvents the need for an ultrasonic waveguide in detecting/receiving signals. Additionally, using a laser vibrometer 75 enables the use of fibre optic cables, which may be well suited to situations where access is limited. A degree of curvature could be incorporated into a waveguide 88 to address access problems but, as discussed in relation to the first embodiment, the allowable degree of curvature would be limited by the wavelength of the input wave.

The invention addresses the discussed problems with the prior art by reducing the footprint of the inspection device to allow access to confined spaces and/or to provide a small and highly focussed contact point for applying energy to set up vibrations in a component. The complexity of the arm mechanism is also minimised, meaning it can be more easily shaped to fit awkward geometries and tight spaces.

As set out above, the size and shape of the components of an aero engine make access and inspection extremely difficult. Even where individual stages of a compressor are considered, certain elements such as seal fins can be sized and spaced such that direct access is impossible with a contact probe/transducer. In these cases, the only option currently available is to rely on FPI and ECT to inspect these areas.

The invention advantageously allows the inspection of coated seal fins on gas turbine engine components, saving the significant cost and time associated with removing and reapplying a coating as is required for FPI and ECT.

The invention removes the need to have direct contact between the transducer and component during a contact ultrasonic inspection, while still allowing the use of contact UT techniques. The contact footprint at the end of the elongate connector, or 'arm', can be made extremely small without compromising the power or quality of the transducer, and the contact face can be easily angled or twisted to a desired angle. This gives a user the ability to inject ultrasonic signals into, and receive them from, the component at very specific locations and orientations. As a result, the need to rely on FPI and ECT, which can be influenced by the coating on the component, can be avoided in a far greater number of instances, or even eliminated altogether.

The invention allows greater flexibility in the direction in which the acoustic wave is sent owing to greater flexibility in the shape/design of the elongate connector 52 88, which can be realised as an inexpensive component that is easily machined to a required form. The connector can twist and/or curve in multiple dimensions, provided the curve radius not too great to damage wave propagation. Swapping of transducers during an inspection operation, when required, can be carried out without the need to remove the elongate connector.

The elongate connector, or 'arm' 52, can be almost any shape necessary to obtain access to the desired location(s). Indeed, the elongate connector 52,88 can be made from a suitable flexible non-acoustically attenuative material (e.g. shape memory alloy) that could be dynamically formed to yield access to difficult-to-reach areas. This would allow a single instrument to inspect several different geometries, including ones more complex than those shown in FIGS. 3 and 4. As an alternative to using more exotic materials, lockable joints could be implemented at strategic positions along the arm 52 to provide a similar benefit. The joints would be designed to maximise acoustic transmission when locked, but still allow sufficient flexibility during deployment when unlocked.

The present invention was developed in response to a need arising specifically in the field of aero engines. However, it should be apparent that it would also be applicable in many other situations where features/components need to be inspected ultrasonically but where access is limited/difficult, e.g. the ultrasonic inspection of an internal bracket on a ship. Modifications to the shape of the elongate connector may be required depending on the application, but the underlying principles remain the same.

The invention claimed is:

1. A method of inspecting a component, the method comprising the steps of:
spacing an ultrasonic transducer from a contact head, using an elongate connector arranged between the transducer and the contact head, wherein the elongate connector carries soundwaves produced by the transducer between the transducer and the contact head;
placing the contact head into contact with a surface of the component to be tested, where the component is annular and comprises at least one sharp edge;
transmitting a wavepacket signal from the transducer along the elongate connector and into the component to be tested to excite a flexural wave in the at least one sharp edge; and
monitoring for reflection of the signal from within the component using a detector; wherein
the contact head is placed into contact with the component adjacent the at least one sharp edge.

2. The method according to claim 1, wherein the detector monitors the deflection of an edge of the sharp edged component.

3. The method according to claim 2, wherein the detector is spaced from the contact head.

4. The method according to claim 2, wherein the detector comprises a laser vibrometer.

5. The method according to claim 3, wherein a defect is detected when the detector first detects an incident wave directly generated in the component by the signal from the transducer and subsequently detects a reflected wave of similar magnitude to the incident wave.

6. The method according to claim 3, wherein the detector comprises a laser vibrometer.

7. The method according to claim 1, wherein the detector monitors an area that is no more than 1 mm wide.

8. The method according to claim 1, further comprising the step of transmitting coupling media to the interface between the contact head and the component to be tested.

9. The method according to claim 1, wherein, during inspection, the contact head is held in a fixed position on the component to be inspected.

10. The method according to claim 1, wherein the soundwaves comprise a signal with a frequency from 500 kHz to 2 MHz.

11. The method according to claim 1, wherein the annular component is a seal fin.

12. An ultrasonic testing apparatus comprising:
a transducer,
a contact head, configured to contact a component being tested, wherein
the component is annular and comprises at least one sharp edge, and
the contact head is configured to contact the component being tested adjacent the at least one sharp edge, and
an elongate connector arranged between the transducer and the contact head to space the transducer from the component,
wherein the elongate connector carries soundwaves produced by the transducer between the transducer and the contact head such that a flexural wave is excited in the at least one sharp edge.

13. The ultrasonic testing apparatus according to claim 12, wherein the contact head and/or the elongate connector comprise a damping or acoustic matching material.

* * * * *